(12) United States Patent
Pianca (10) Patent No.: US 10,709,888 B2
(45) Date of Patent: Jul. 14, 2020

(54) SYSTEMS AND METHODS FOR MAKING AND USING AN ELECTRICAL STIMULATION SYSTEM FOR PERIPHERAL NERVE STIMULATION

(71) Applicant: Boston Scientific Neuromodulation Corporation, Valencia, CA (US)

(72) Inventor: Anne Margaret Pianca, Santa Monica, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 131 days.

(21) Appl. No.: 15/656,734

(22) Filed: Jul. 21, 2017

(65) Prior Publication Data

US 2018/0028804 A1 Feb. 1, 2018

Related U.S. Application Data

(60) Provisional application No. 62/368,658, filed on Jul. 29, 2016.

(51) Int. Cl.
*A61N 1/05* (2006.01)
*A61B 17/34* (2006.01)
(Continued)

(52) U.S. Cl.
CPC ........ *A61N 1/0551* (2013.01); *A61B 17/3468* (2013.01); *A61N 1/36071* (2013.01);
(Continued)

(58) Field of Classification Search
CPC . A61N 1/05; A61N 1/36; A61N 1/372; A61N 1/0551; A61N 1/36007; A61N 1/00;
(Continued)

(56) References Cited

U.S. PATENT DOCUMENTS 3,769,984 A 11/1973 Muench
3,941,136 A 3/1976 Bucalo
(Continued)

FOREIGN PATENT DOCUMENTS

EP 0234457 A2 9/1987
EP 0778047 A2 6/1997
(Continued)

OTHER PUBLICATIONS

Rozman et al., "Selective Stimulation of Autonomic Nerves and Recording of Electroneurograms in a Canine Model," Artificial Organs, 21(8): 592-596, 2008.
(Continued)

*Primary Examiner* — George J Ulsh
(74) *Attorney, Agent, or Firm* — Lowe Graham Jones PLLC; Bruce E. Black (57) ABSTRACT

An electrical stimulation lead includes a lead body; a terminal disposed along the proximal end portion of the lead body; a single electrode disposed at the distal end of the lead body; a conductor extending along the lead body and electrically coupling the terminal to the single electrode; and an adjustable sheath disposed over a portion of the lead body to cover a selected portion of the single electrode by displacing the sheath forwards or backwards relative to the single electrode to control a size of a portion of the electrode exposed for stimulation of tissue. Another electrical stimulation lead has a low-profile distal portion that has a smaller lateral width in at least one direction than a remainder of the lead body. Yet another arrangement includes a guidewire with a mapping electrode to map a region around a peripheral nerve prior to implantation of an electrical stimulation lead.

20 Claims, 7 Drawing Sheets

(51) Int. Cl.
*A61N 1/36* (2006.01)
*A61N 1/372* (2006.01)
*A61N 1/378* (2006.01)

(52) U.S. Cl.
CPC ....... *A61N 1/36185* (2013.01); *A61N 1/3787* (2013.01); *A61N 1/37229* (2013.01); *A61N 1/37235* (2013.01); *A61N 1/3605* (2013.01); *A61N 1/36007* (2013.01); *A61N 1/36062* (2017.08); *A61N 1/36107* (2013.01); *A61N 1/372* (2013.01)

(58) Field of Classification Search
CPC .............. A61N 1/3605; A61N 1/36107; A61N 1/36185; A61N 1/37229; A61N 1/37235; A61B 18/00
See application file for complete search history.

(56) References Cited

U.S. PATENT DOCUMENTS

| | | |
|---|---|---|
| 4,033,357 A | 7/1977 | Helland et al. |
| 4,135,518 A | 1/1979 | Dutcher |
| 4,257,428 A | 3/1981 | Barton et al. |
| 4,301,815 A | 11/1981 | Doring |
| 4,409,994 A | 10/1983 | Doring |
| 4,475,560 A | 10/1984 | Tarjan et al. |
| 4,506,679 A | 3/1985 | Mann |
| 4,542,753 A | 9/1985 | Brenman et al. |
| 4,585,005 A | 4/1986 | Lue et al. |
| 4,628,944 A | 12/1986 | MacGregor et al. |
| 4,702,254 A | 10/1987 | Zabara |
| 4,716,888 A | 1/1988 | Wesner |
| 4,722,353 A | 2/1988 | Sluetz |
| 4,735,205 A * | 4/1988 | Chachques ........ A61N 1/36003 607/2 |
| 4,796,643 A | 1/1989 | Nakazawa et al. |
| 4,867,164 A | 9/1989 | Zabara |
| 4,920,979 A | 5/1990 | Bullara |
| 4,934,368 A | 6/1990 | Lynch |
| 4,957,118 A | 9/1990 | Erlebacher |
| 5,025,807 A | 6/1991 | Zabara |
| 5,095,905 A | 3/1992 | Klepinski |
| 5,139,539 A | 8/1992 | Haynes, Jr. |
| 5,143,067 A | 9/1992 | Rise et al. |
| 5,193,539 A | 3/1993 | Schulman et al. |
| 5,193,540 A | 3/1993 | Schulman et al. |
| 5,239,540 A | 8/1993 | Rovira et al. |
| 5,251,634 A | 10/1993 | Weinberg |
| 5,257,634 A | 11/1993 | Kroll |
| 5,282,468 A | 2/1994 | Klepinski |
| 5,312,439 A | 5/1994 | Loeb |
| 5,314,457 A | 5/1994 | Jeutter et al. |
| 5,324,322 A | 6/1994 | Grill et al. |
| 5,324,327 A | 6/1994 | Cohen |
| 5,376,108 A | 12/1994 | Collins et al. |
| 5,405,367 A | 4/1995 | Schulman et al. |
| 5,423,876 A * | 6/1995 | Camps .................... A61N 1/05 607/116 |
| 5,433,735 A | 7/1995 | Zanakis et al. |
| 5,439,938 A | 8/1995 | Synder et al. |
| 5,454,840 A | 10/1995 | Krakovsky et al. |
| 5,480,420 A | 1/1996 | Hoegnelid et al. |
| 5,487,756 A | 1/1996 | Kallesoe et al. |
| 5,531,781 A | 7/1996 | Alferness et al. |
| 5,571,118 A | 11/1996 | Boutos |
| 5,741,319 A | 4/1998 | Woloszko et al. |
| 5,755,762 A | 5/1998 | Bush |
| 5,775,331 A | 7/1998 | Raymond et al. |
| 5,871,530 A | 2/1999 | Williams et al. |
| 5,876,399 A | 3/1999 | Chia et al. |
| 5,919,220 A | 7/1999 | Stieglitz et al. |
| 5,919,222 A | 7/1999 | Hjelle et al. |
| 5,922,015 A | 7/1999 | Schaldach et al. |
| 5,938,584 A | 8/1999 | Ardito et al. |
| 6,051,017 A | 4/2000 | Loeb et al. |
| 6,058,332 A | 5/2000 | Dahl |
| 6,061,596 A | 5/2000 | Richmond et al. |
| 6,151,526 A | 11/2000 | Tziviskos |
| 6,175,710 B1 | 1/2001 | Kamaji et al. |
| 6,175,764 B1 | 1/2001 | Loeb et al. |
| 6,181,965 B1 | 1/2001 | Loeb et al. |
| 6,181,969 B1 | 1/2001 | Fielding et al. |
| 6,181,973 B1 | 1/2001 | Ceron et al. |
| 6,185,452 B1 | 2/2001 | Schulman et al. |
| 6,185,455 B1 | 2/2001 | Loeb et al. |
| 6,188,932 B1 | 2/2001 | Lindegren |
| 6,201,994 B1 | 3/2001 | Warman et al. |
| 6,214,032 B1 | 4/2001 | Loeb et al. |
| 6,224,450 B1 | 5/2001 | Norton |
| 6,271,094 B1 | 8/2001 | Boyd et al. |
| 6,278,897 B1 | 8/2001 | Rutten et al. |
| 6,292,703 B1 | 9/2001 | Meier et al. |
| 6,295,944 B1 | 10/2001 | Lovett |
| 6,308,105 B1 | 10/2001 | Duysens et al. |
| 6,315,721 B2 | 11/2001 | Schulman et al. |
| 6,364,278 B1 | 4/2002 | Lin et al. |
| 6,391,985 B1 | 5/2002 | Goode et al. |
| 6,456,866 B1 | 9/2002 | Tyler et al. |
| 6,463,335 B1 | 10/2002 | Munch et al. |
| 6,516,227 B1 | 2/2003 | Meadows et al. |
| 6,582,441 B1 | 6/2003 | He et al. |
| 6,584,363 B2 | 6/2003 | Heil, Jr. et al. |
| 6,609,029 B1 | 8/2003 | Mann et al. |
| 6,609,032 B1 | 8/2003 | Woods et al. |
| 6,643,546 B2 | 11/2003 | Mathis et al. |
| 6,650,943 B1 | 11/2003 | Whitehurst et al. |
| 6,735,474 B1 | 5/2004 | Loeb et al. |
| 6,741,892 B1 | 5/2004 | Meadows et al. |
| 6,788,975 B1 | 9/2004 | Whitehurst et al. |
| 7,003,352 B1 | 2/2006 | Whitehurst |
| 7,006,875 B1 | 2/2006 | Kuzma et al. |
| 7,203,548 B2 | 4/2007 | Whitehurst et al. |
| 7,244,150 B1 | 7/2007 | Brase et al. |
| 7,248,930 B1 | 7/2007 | Woloszko et al. |
| 7,292,890 B2 | 11/2007 | Whitehurst et al. |
| 7,437,193 B2 | 10/2008 | Parramon et al. |
| 7,450,997 B1 | 11/2008 | Pianca et al. |
| 7,460,913 B2 | 12/2008 | Kuzma et al. |
| 7,584,004 B2 | 9/2009 | Caparso et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,706,892 B2 | 4/2010 | Colvin et al. |
| 7,761,165 B1 | 7/2010 | He et al. |
| 7,783,359 B2 | 8/2010 | Meadows |
| 7,783,362 B2 | 8/2010 | Whitehurst et al. |
| 7,792,590 B1 | 9/2010 | Pianca et al. |
| 7,809,446 B2 | 10/2010 | Meadows |
| 7,840,279 B2 | 11/2010 | He |
| 7,949,395 B2 | 5/2011 | Kuzma |
| 7,953,498 B1 | 5/2011 | Carbunaru et al. |
| 7,974,706 B2 | 7/2011 | Moffitt et al. |
| 8,019,443 B2 | 9/2011 | Schleicher et al. |
| 8,155,757 B1 | 4/2012 | Neisz et al. |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,364,278 B2 | 1/2013 | Pianca et al. |
| 8,391,985 B2 | 3/2013 | McDonald |
| 8,483,237 B2 | 7/2013 | Zimmermann et al. |
| 8,594,805 B2 | 11/2013 | Hincapie Ordonez et al. |
| 8,612,025 B2 | 12/2013 | Neisz et al. |
| 8,688,235 B1 | 4/2014 | Pianca et al. |
| 8,718,790 B2 | 5/2014 | Pianca |
| 8,768,488 B2 | 7/2014 | Barker |
| 8,818,524 B2 | 8/2014 | Hincapie Ordonez et al. |
| 8,831,742 B2 | 9/2014 | Pianca et al. |
| 8,849,422 B2 | 9/2014 | Pianca |
| 8,934,992 B2 | 1/2015 | Johnson et al. |
| 2002/0022873 A1 * | 2/2002 | Erickson ............ A61B 5/0422 607/117 |
| 2003/0040785 A1 | 2/2003 | Maschino et al. |

(56) References Cited

U.S. PATENT DOCUMENTS

| | | |
|---|---|---|
| 2003/0045919 A1 | 3/2003 | Swoyer et al. |
| 2003/0074039 A1 | 4/2003 | Puskas |
| 2003/0078623 A1 | 4/2003 | Weinberg et al. |
| 2003/0114905 A1 | 6/2003 | Kuzma |
| 2003/0199938 A1 | 10/2003 | Smits et al. |
| 2003/0236558 A1 | 12/2003 | Whitehurst et al. |
| 2004/0010303 A1 | 1/2004 | Bolea et al. |
| 2004/0034401 A1 | 2/2004 | Dahlberg et al. |
| 2004/0059392 A1 | 3/2004 | Parramon et al. |
| 2004/0111139 A1 | 6/2004 | McCreery |
| 2004/0230280 A1 | 11/2004 | Cates et al. |
| 2005/0010265 A1 | 1/2005 | Baru Fassio et al. |
| 2005/0065589 A1 | 3/2005 | Schneider et al. |
| 2005/0177220 A1 | 8/2005 | Iaizzo et al. |
| 2005/0182472 A1 | 8/2005 | Wahlstrom et al. |
| 2006/0161204 A1 | 7/2006 | Colvin et al. |
| 2006/0184204 A1 | 8/2006 | He |
| 2006/0212075 A1 | 9/2006 | Marnfeldt |
| 2006/0241737 A1 | 10/2006 | Tockman et al. |
| 2006/0282145 A1 | 12/2006 | Caparso et al. |
| 2007/0150036 A1 | 6/2007 | Anderson |
| 2007/0219595 A1 | 9/2007 | He |
| 2008/0046055 A1 | 2/2008 | Durand et al. |
| 2008/0071320 A1 | 3/2008 | Brase |
| 2009/0118727 A1 | 5/2009 | Pearson et al. |
| 2009/0187222 A1 | 7/2009 | Barker |
| 2009/0276021 A1 | 11/2009 | Meadows et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0049276 A1 | 2/2010 | Blum et al. |
| 2010/0076535 A1 | 3/2010 | Pianca et al. |
| 2010/0241207 A1 | 9/2010 | Bluger |
| 2010/0268298 A1 | 10/2010 | Moffitt et al. |
| 2010/0298916 A1 | 11/2010 | Rabischong et al. |
| 2011/0004267 A1 | 1/2011 | Meadows et al. |
| 2011/0005069 A1 | 1/2011 | Pianca |
| 2011/0078900 A1 | 4/2011 | Pianca et al. |
| 2011/0130803 A1 | 6/2011 | McDonald |
| 2011/0130817 A1 | 6/2011 | Chen |
| 2011/0130818 A1 | 6/2011 | Chen |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0316615 A1 | 12/2012 | Digiore et al. |
| 2013/0023974 A1 | 1/2013 | Amrani |
| 2013/0105071 A1 | 5/2013 | Digiore et al. |
| 2013/0172973 A1 | 7/2013 | Tockman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317518 A1 | 11/2013 | Govea |
| 2013/0317587 A1 | 11/2013 | Barker |
| 2013/0325091 A1 | 12/2013 | Pianca et al. |
| 2014/0039587 A1 | 2/2014 | Romero |
| 2014/0074213 A1 | 3/2014 | Neisz et al. |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0202433 A1 | 7/2015 | Franke et al. |
| 2015/0202446 A1 | 7/2015 | Franke et al. |
| 2015/0366467 A1 | 12/2015 | De Kock et al. |
| 2017/0224982 A1 | 8/2017 | Nageri et al. |

FOREIGN PATENT DOCUMENTS

| | | |
|---|---|---|
| WO | 98/37926 | 9/1998 |
| WO | 98/43700 | 10/1998 |
| WO | 98/43701 | 10/1998 |
| WO | 2008019483 | 2/2008 |
| WO | 2008048471 | 4/2008 |
| WO | 2013188871 | 12/2013 |

OTHER PUBLICATIONS

Polasek et al., "Stimulation Stability and Selectivity of Chronically Implanted Multicontact Nerve Cuff Electrodes in the Human Upper Extremity." IEEE Transactions on Neural Systems and Rehabilitation Engineering, vol. 17, No. 5, 428-437, Oct. 2009.

Plachta et al., "Blood pressure control with selective vagal nerve stimulation and minimal side effects," J. Neural Eng. 11 (2014) 036011 (15pp), 2014.

International Search Report and Written Opinion for PCT/US2017/043333 dated Jan. 5, 2018.

Rattay, F., "Analysis of Models for External Stimulation of Axons," IEEE Transactions on Biomedical Engineering, BME-33(10): 974-977, 1986.

U.S. Appl. No. 15/601,838, filed May 22, 2017.
U.S. Appl. No. 15/436,544, filed Feb. 17, 2017.
U.S. Appl. No. 62/429,650, filed Dec. 2, 2016.
U.S. Appl. No. 15/656,734, filed Jul. 21, 2017.
U.S. Appl. No. 15/608,573, filed May 30, 2017.

\* cited by examiner

SYSTEMS AND METHODS FOR MAKING AND USING AN ELECTRICAL STIMULATION SYSTEM FOR PERIPHERAL NERVE STIMULATION

CROSS-REFERENCE TO RELATED APPLICATIONS

This application claims the benefit under 35 U.S.C. § 119(e) of U.S. Provisional Patent Application Ser. No. 62/368,658, filed Jul. 29, 2016, which is incorporated herein by reference.

FIELD

The present invention is directed to the area of implantable electrical stimulation systems and methods of making and using the systems. The present invention is also directed to electrical stimulation systems for stimulation of peripheral nerves, as well as methods of making and using the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Sacral nerve stimulation has been used to treat incontinence, as well as a number of other applications under investigation. Peripheral nerve stimulation can be used to treat a variety of disorders in the extremities, face, neck, head, abdomen, pelvis, trunk, and other portions of the body including, but not limited to, pain, incontinence, sexual dysfunction, headache, migraine, tremor, and the like.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead that includes a lead body having a proximal end portion and a distal end; a terminal disposed along the proximal end portion of the lead body; a single electrode disposed at the distal end of the lead body; a conductor extending along the lead body and electrically coupling the terminal to the single electrode; and an adjustable sheath disposed over a portion of the lead body to cover a selected portion of the single electrode by displacing the sheath forwards or backwards relative to the single electrode to control a size of a portion of the electrode exposed for stimulation of tissue.

In at least some embodiments, the electrical stimulation lead further includes adhesive for application to the sheath and lead body or single electrode to fix the sheath to the lead body or single electrode after covering the selected portion of the single electrode.

In at least some embodiments, the electrical stimulation lead has a diameter in a range of 0.020 inch to 0.040 inch. In at least some embodiments, the single electrode is configured and arranged to be cut by a user. In at least some embodiments, the single electrode is a solid cylinder of metal. In at least some embodiments, the sheath is made of silicone, polyurethane, polyether ether ketone, polytetrafluoroethylene, polyimide, or a combination thereof.

Another embodiment is an electrical stimulation lead that includes a lead body having a proximal end portion and a distal end portion, where the distal end portion has a smaller lateral width in at least one direction than a remainder of the lead body; at least one terminal disposed along the proximal end portion of the lead body; at least one electrode disposed at the distal end of the lead body; and at least one conductor extending along the lead body and electrically coupling the at least one terminal to the at least one electrode.

In at least some embodiments, the distal end portion has a circular cross-section. In at least some embodiments, the distal end portion of the electrical stimulation lead has a diameter of 0.020 inch or less. In at least some embodiments, the remainder of the electrical stimulation lead has a diameter of at least 0.040 inch.

In at least some embodiments, the distal end portion has a cross-section with a major axis width and a minor axis width of different values. In at least some embodiments, the minor axis width of the distal end portion of the electrical stimulation lead has a value of 0.020 inch or less.

In at least some embodiments, the at least one electrode is a plurality of electrodes. In at least some embodiments, at least one of the at least one electrode does not extend around a full perimeter of the distal end portion of the electrical stimulation lead.

Yet another embodiment is a kit for implanting a lead for stimulation of a peripheral nerve of a patient. The kit includes a guidewire with an electrode disposed at a distal end of the guidewire; an introducer having a lumen for receiving the guidewire; and a lead including a lead body and at least one electrode disposed along a distal portion of the lead body, the lead body defining a lumen for receiving the guidewire.

A further embodiment is a method for implanting a lead for stimulation of a peripheral nerve of a patient using the kit described above. The method includes advancing a distal portion of the guidewire using the introducer to a position adjacent the peripheral nerve; mapping a region around the peripheral nerve using the electrode of the guidewire; optionally removing the introducer; and advancing the lead over the guidewire, with a portion of the guidewire disposed in the lumen of the lead, to position the at least one electrode of the lead adjacent the peripheral nerve.

In at least some embodiments, mapping the region around the peripheral nerve includes stimulation patient tissue using the electrode of the guidewire. In at least some embodiments, mapping the region around the peripheral nerve includes receiving electrical signals from patient tissue using the electrode of the guidewire. In at least some embodiments, the introducer is no more than 20 gauge. In at least some embodiments, the method further includes repositioning the distal portion of the guidewire to another site relative to the peripheral nerve.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to electrical stimulation systems for stimulation of peripheral nerves, as well as methods of making and using the electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

Figure 1A:
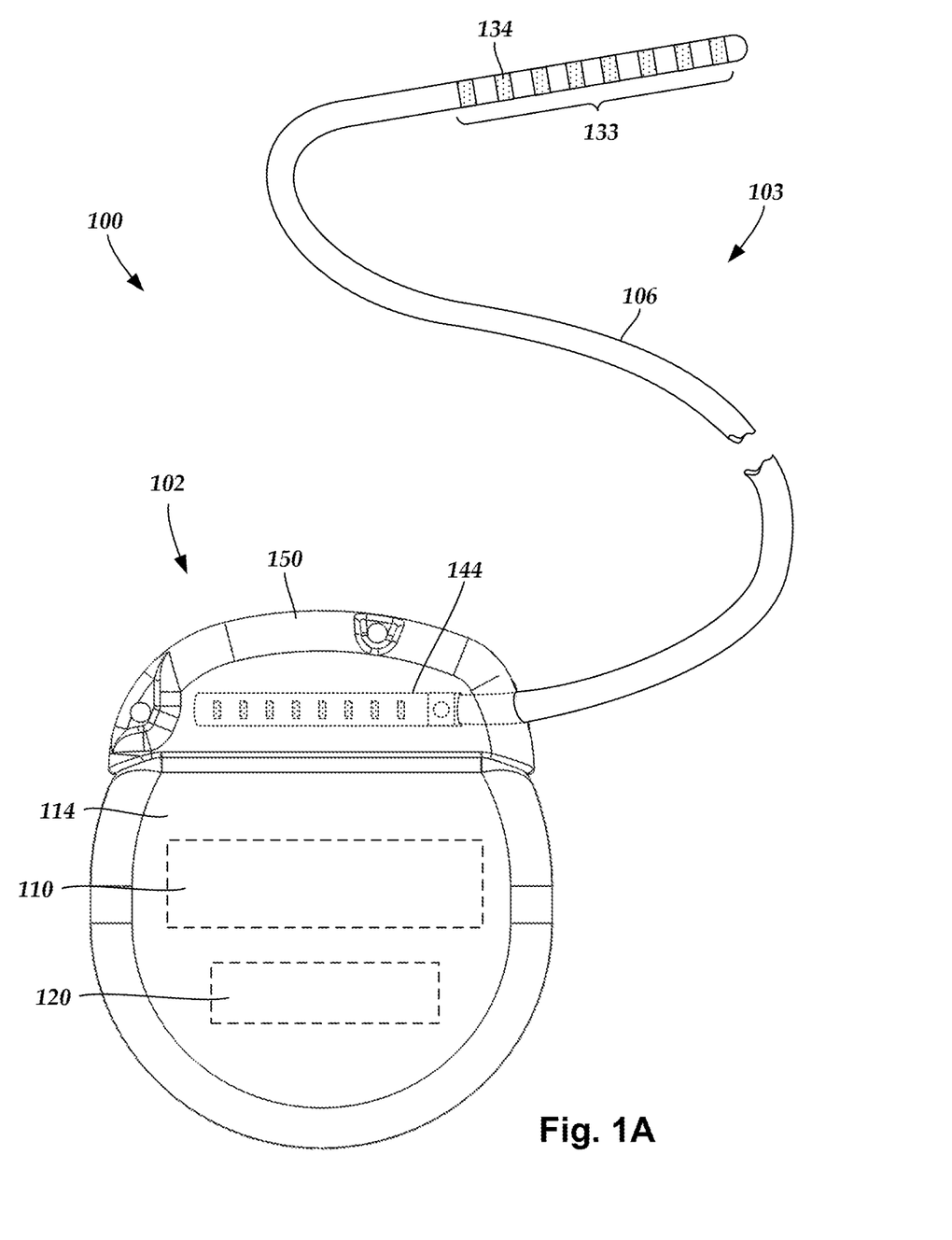
FIG. 1A is a schematic view of one embodiment of an electrical stimulation system that includes a percutaneous lead body coupled to a control module, according to the invention.

FIG. 1A illustrates schematically one embodiment of an electrical stimulation system 100. The electrical stimulation system 100 includes a control module (e.g., a stimulator or pulse generator) 102 and a percutaneous lead 103. The lead 103 includes a plurality of electrodes 134 that form an array of electrodes 133. The control module 102 typically includes an electronic subassembly 110 and an optional power source 120 disposed in a sealed housing 114. In some embodiments, the control module 102 can be a microstimulator.

Figure 1B:
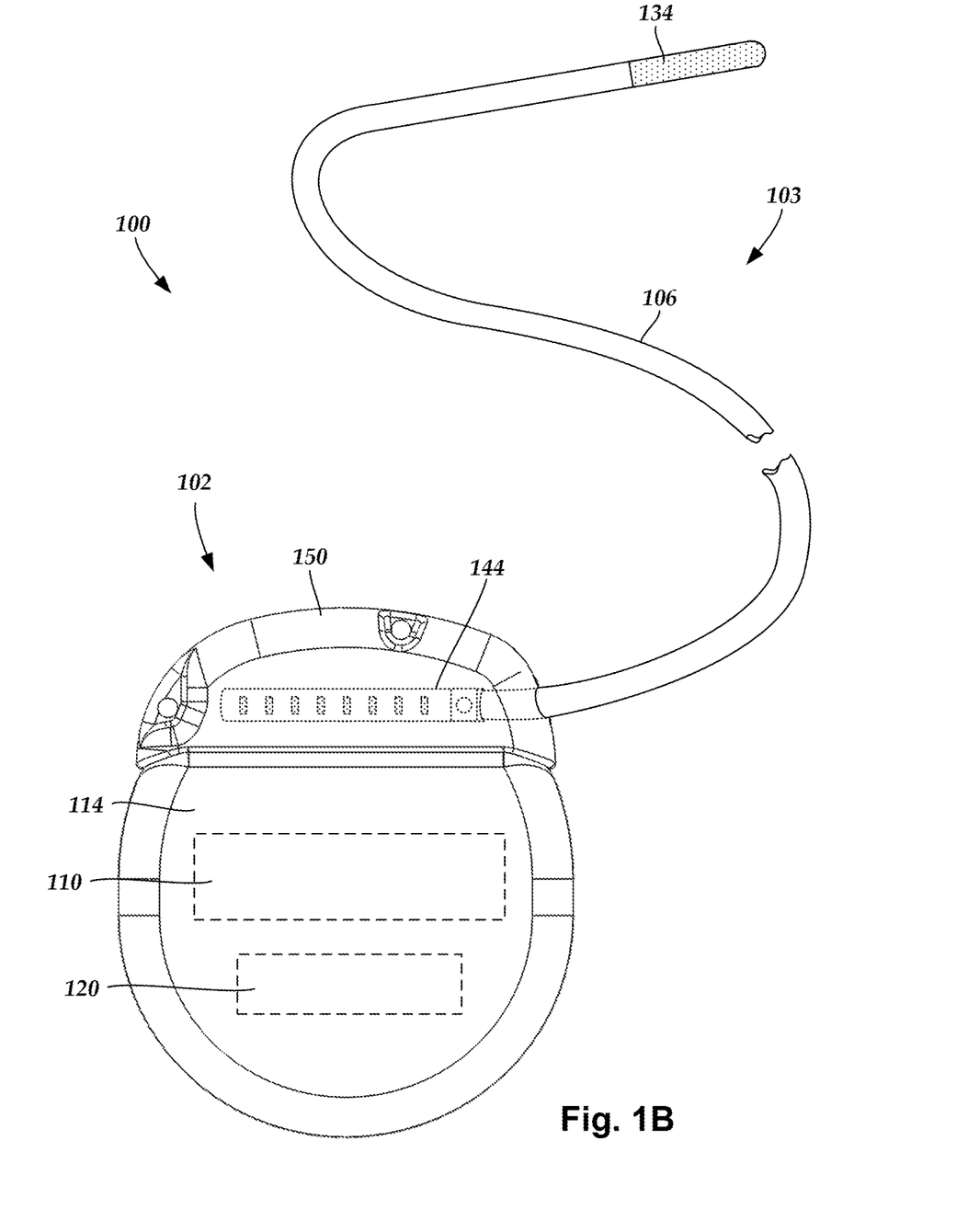
FIG. 1B is a schematic view of another embodiment of an electrical stimulation system that includes a percutaneous lead body with a single electrode coupled to a control module, according to the invention.

The lead 103 includes a lead body 106 coupling the control module 102 to the plurality of electrodes 134. In at least some embodiments, the lead body 106 is isodiametric. FIG. 1B illustrates another embodiment of an electrical stimulation system 100 except that the lead 103 includes a single electrode 134.

The control module 102 typically includes one or more connector assemblies 144 into which the proximal end of the lead body 106 can be plugged to make an electrical connection via connector contacts (e.g., 216 in FIG. 2A) disposed in the connector assembly 144 and terminals (e.g., 210 in FIG. 2A) disposed along the lead body 106. The connector contacts are coupled to the electronic subassembly 110 and the terminals are coupled to the electrodes 134. Optionally, the control module 102 may include a plurality of connector assemblies 144. In other embodiments, the lead may be permanently connected to the control module.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 224 (see FIG. 2B) can be disposed between the lead body 106 and the control module 102 to extend the distance between the lead body 106 and the control module 102.

The electrical stimulation system or components of the electrical stimulation system, including the lead body 106 and the control module 102, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, or titanium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1A, eight electrodes 134 are shown. In FIG. 1B, a single electrode 134 is shown. The electrodes 134 can be formed in any suitable shape including, for example, round, oval, triangular, rectangular, pentagonal, hexagonal, heptagonal, octagonal, or the like. In the illustrated lead of FIG. 1A, the electrodes are ring electrodes. In the illustrated lead of FIG. 1B, the electrode is a tip electrode. It will be understood that other electrodes can also be used including sets of segmented electrodes that are arranged around the circumference of the lead and facilitate directional stimulation.

The electrodes of the lead body 106 are typically disposed in, or separated by, a non-conductive, biocompatible material including, for example, silicone, polyurethane, and the like or combinations thereof. The lead body 106 may be formed in the desired shape by any process including, for example, extruding, molding (including injection molding), casting, and the like. Electrodes and connecting wires can be disposed onto or within a lead body either prior to or subsequent to a molding or casting process. The non-conductive material typically extends from the distal end of the lead body 106 to the proximal end of the lead body 106.

Terminals (e.g., 210 in FIG. 2A) are typically disposed at the proximal end of the lead body 106 for connection to corresponding conductive contacts (e.g., 216 in FIG. 2A) in one or more connector assemblies (e.g., 144 in FIG. 1A) disposed on, for example, the control module 102 (or to other devices, such as conductive contacts on a lead extension, an operating room cable, a splitter, an adaptor, or the like).

Conductive wires extend from the plurality of terminals (see e.g., 210 in FIG. 2A) to the plurality of electrodes 133. Typically, each of the plurality of terminals is electrically coupled to at least one of the plurality of electrodes 133. In some embodiments, each of the plurality of terminals is coupled to a single electrode 134 of the plurality of electrodes 133.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the lead 103. The one or more lumens may, optionally, be flushed continually, or on a regular basis, with saline, or the like. The one or more lumens can be permanently or removably sealable at the distal end.

As discussed above, the lead body 106 may be coupled to the one or more connector assemblies 144 disposed on the control module 102. The control module 102 can include any suitable number of connector assemblies 144 including, for example, one, two, three, four, five, six, seven, eight, or more connector assemblies 144. It will be understood that other numbers of connector assemblies 144 may be used instead. In FIG. 1A, the lead body 106 includes eight terminals that are shown coupled with eight conductive contacts disposed in the connector assembly 144.

Figure 2A:
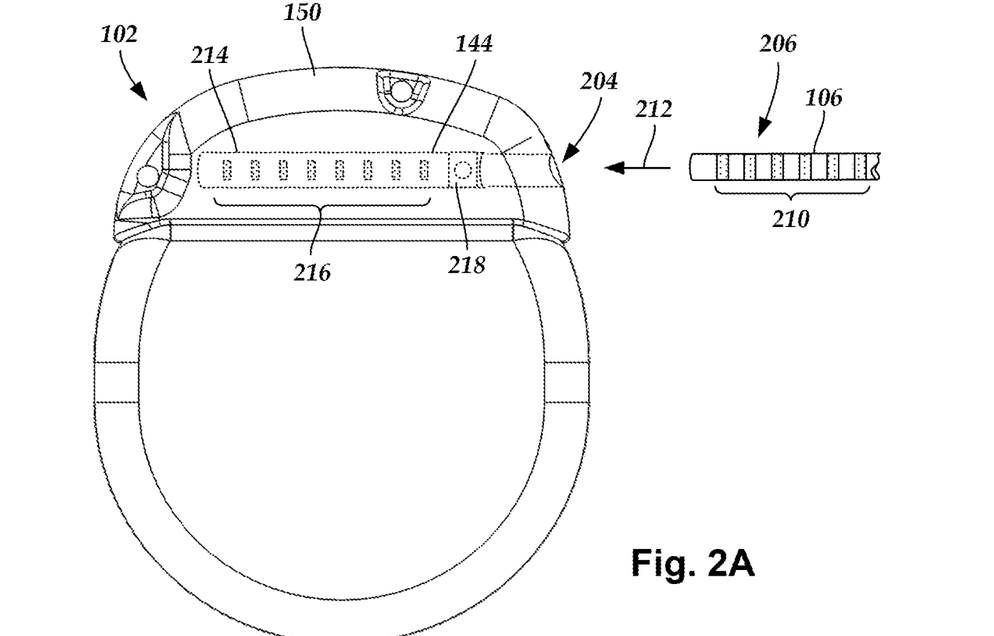
FIG. 2A is a schematic view of one embodiment of a plurality of connector assemblies disposed in the control module of FIG. 1a, the connector assemblies configured and arranged to receive the proximal portions of the lead bodies of FIG. 1a, according to the invention.

FIG. 2A is a schematic side view of one embodiment of a connector assembly 144 disposed on the control module 102. In FIG. 2A, the proximal end 206 of the lead body 106 is shown configured and arranged for insertion to the control module 102.

In FIG. 2A, the connector assembly 144 is disposed in the header 150. In at least some embodiments, the header 150 defines a port 204 into which the proximal end 206 of the lead body 106 with terminals 210 can be inserted, as shown by directional arrows 212, in order to gain access to the connector contacts disposed in the connector assembly 144.

The connector assembly 144 includes a connector housing 214 and a plurality of connector contacts 216 disposed therein. Typically, the connector housing 214 defines a port (not shown) that provides access to the plurality of connector contacts 216. In at least some embodiments, the connector assembly 144 further includes a retaining element 218 configured and arranged to fasten the corresponding a lead retention sleeve or lead body 106 to the connector assembly 144 when the lead body 106 is inserted into the connector assembly 144 to prevent undesired detachment of the lead body 106 from the connector assembly 144. For example, the retaining element 218 may include an aperture 220 through which a fastener (e.g., a set screw, pin, or the like) may be inserted and secured against a lead retention sleeve on the inserted lead body 106.

When the lead body 106 is inserted into the port 204, the connector contacts 216 can be aligned with the terminals 210 disposed on the lead body 106 to electrically couple the control module 102 to the electrodes (134 of FIG. 1A) disposed at a distal end of the lead body 106. Examples of connector assemblies in control modules are found in, for example, U.S. Pat. No. 7,244,150 and U.S. Patent Application Publication No. 2008/0071320, which are incorporated by reference.

Figure 2B:
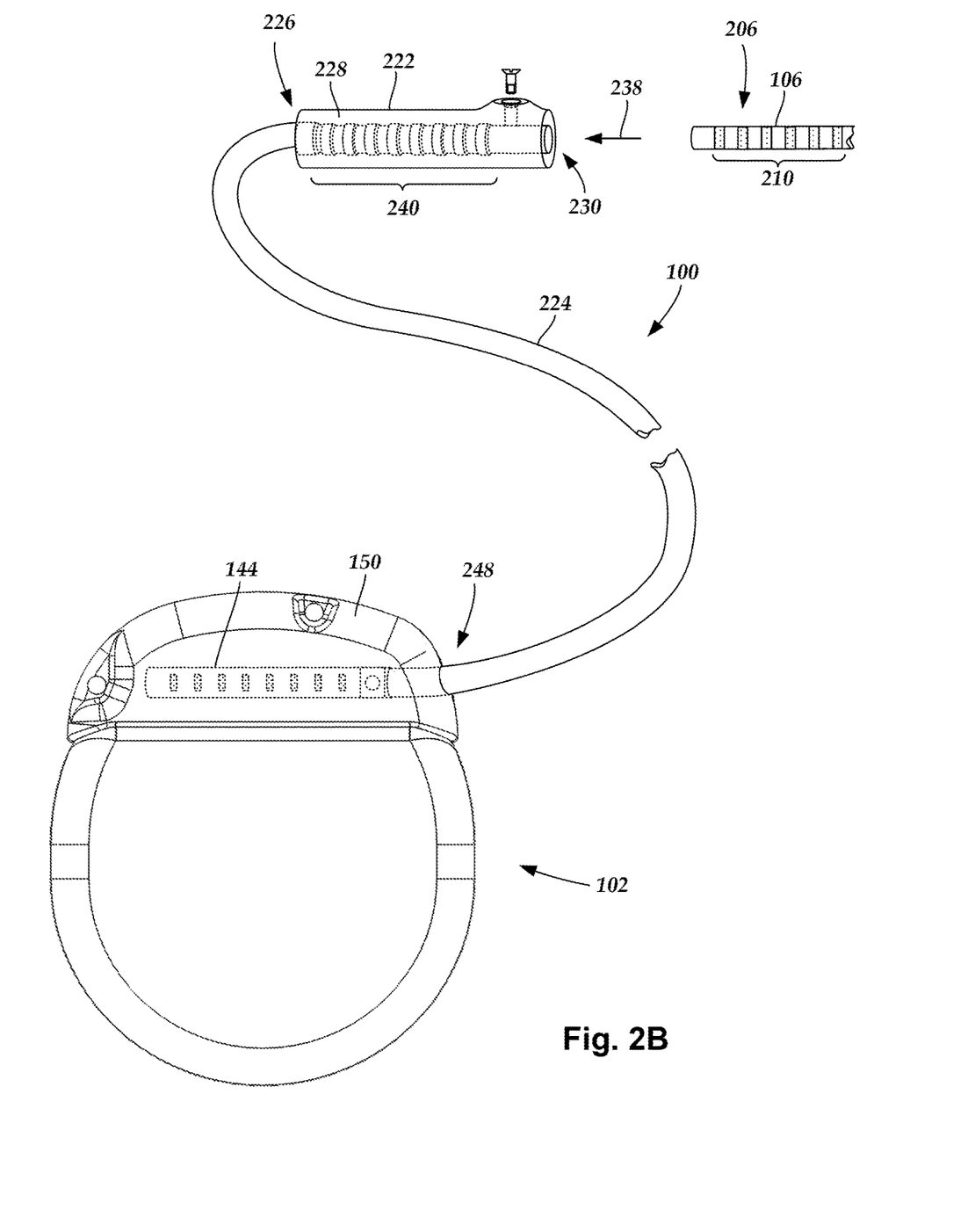
FIG. 2B is a schematic view of one embodiment of a proximal portion of the lead body of FIG. 1A, a lead extension, and the control module of FIG. 1A, the lead extension configured and arranged to couple the lead body to the control module, according to the invention.

In at least some embodiments, the electrical stimulation system includes one or more lead extensions. The lead body 106 can be coupled to one or more lead extensions which, in turn, are coupled to the control module 102. In FIG. 2B, a lead extension connector assembly 222 is disposed on a lead extension 224. The lead extension connector assembly 222 is shown disposed at a distal end 226 of the lead extension 224. The lead extension connector assembly 222 includes a contact housing 228. The contact housing 228 defines at least one port 230 into which a proximal end 206 of the lead body 106 with terminals 210 can be inserted, as shown by directional arrow 238. The lead extension connector assembly 222 also includes a plurality of connector contacts 240. When the lead body 106 is inserted into the port 230, the connector contacts 240 disposed in the contact housing 228 can be aligned with the terminals 210 on the lead body 106 to electrically couple the lead extension 224 to the electrodes (134 of FIG. 1A) disposed at a distal end (not shown) of the lead body 106.

The proximal end of a lead extension can be similarly configured and arranged as a proximal end of a lead body. The lead extension 224 may include a plurality of conductive wires (not shown) that electrically couple the connector contacts 240 to terminal on a proximal end 248 of the lead extension 224. The conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a lead extension connector assembly disposed in another lead extension. In other embodiments (as shown in FIG. 2B), the proximal end 248 of the lead extension 224 is configured and arranged for insertion into the connector assembly 144 disposed on the control module 102.

The systems and methods described below are particularly, although not exclusively, useful for stimulation of peripheral nerves. A peripheral nerve target may be in, for example, the upper extremities, the lower extremities, the head, the neck, the face, the abdomen, the pelvis, or the trunk. The peripheral target depth can vary depending on the specific nerve target (for example, the face versus a limb) and the patient's individual anatomy (for example, depending on weight, height, age, gender, or the like). Furthermore, the volume of stimulation, (as determined by, for example, the electrode array coverage and span and the stimulation parameters) can vary depending on, for example, the nerve target or the individual patient's pain etiology. Some conventional spinal cord stimulation leads have been proposed for use in peripheral nerve stimulation, but such stimulation leads may not provide some of the preferences or advantages describe above or below.

Figure 3A:
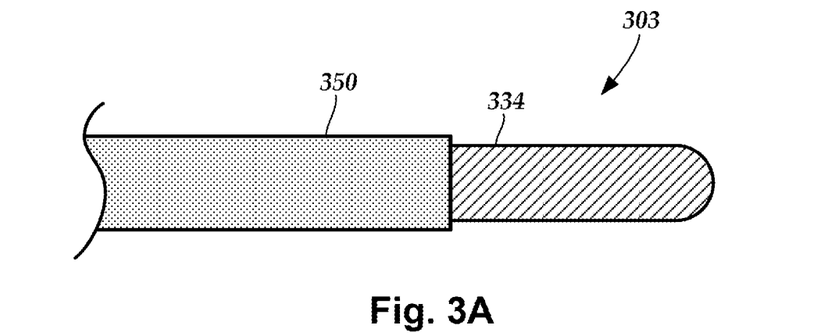
FIG. 3A is a schematic side view of a distal end of one embodiment of a lead having a sheath for covering a portion of an electrode, according to the invention.
Figure 3B:
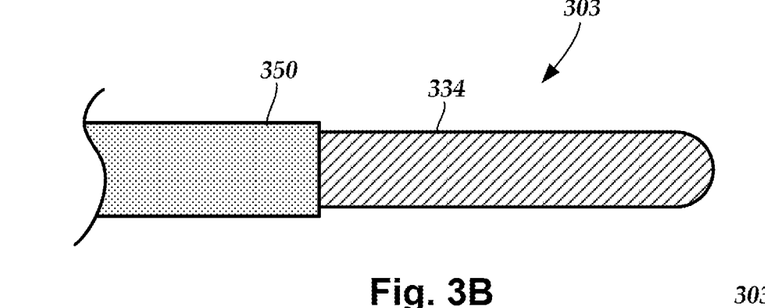
FIG. 3B is a schematic side view of the lead of FIG. 3A with the sheath pulled backward, according to the invention.
Figure 3C:
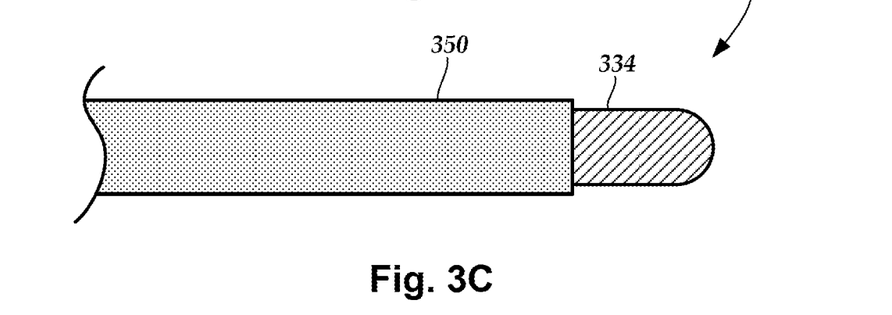
FIG. 3C is a schematic side view of the lead of FIG. 3A with the sheath pulled forward, according to the invention.

FIG. 3A illustrates one embodiment of a distal end of a lead 303 with a single electrode 334 and a non-conductive sheath 350 that can be used to cover a portion of the electrode to provide a customizable electrode length. Such an arrangement also results in a customizable stimulation volume so that a clinician can select the size of the stimulation region by moving the sheath 350 to a desired position along the distal end of the lead 303. FIG. 3B illustrates an arrangement where the sheath 350 has been pulled back relative to the position illustrated in FIG. 3A to expose more of the electrode 334 for an effectively longer electrode and larger stimulation volume. FIG. 3C illustrates an arrangement where the sheath 350 has been pushed forward relative to the position illustrated in FIG. 3A to cover more of the electrode 334 for an effectively shorter electrode and smaller stimulation volume. The sheath can be made out of any suitable, biocompatible material including, but not limited to, silicone, polyurethane, polyether ether ketone, polytetrafluoroethylene (e.g., Teflon™) or other biocompatible fluoropolymers, polyimide or the like or any combination thereof.

In at least some embodiments, the sheath 350 is constructed so that a clinician or surgeon can move the sheath forward or backward from an initial position prior to implantation. In at least some embodiments, the sheath 350 can be adhered to the lead body or electrode 334 with medical adhesive or any other suitable, biocompatible bonding agent including, but not limited to, epoxy, fibrin, cyanoacrylate, any type of biocompatible medical adhesive, or the like.

In at least some embodiments, the lead has a diameter in the range of 0.020 inch-0.040 inch (0.051 to 0.10 cm). In at least some embodiments, the lead has a diameter of no more than 0.020 inch (0.051 cm).

Figure 3D:
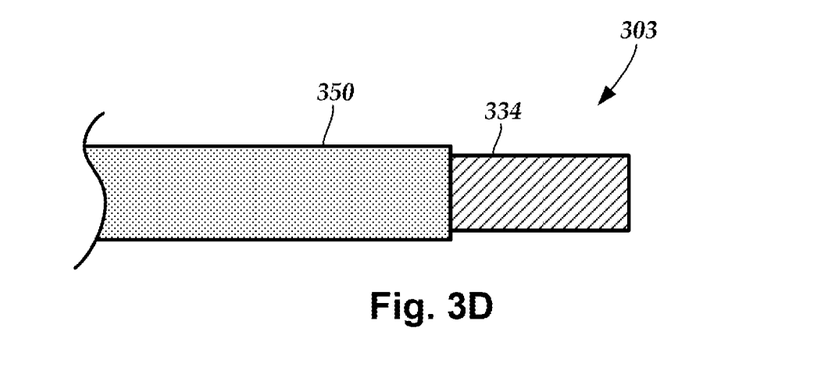
FIG. 3D is a schematic side view of the lead of FIG. 3A with a portion of the electrode cut to reduce a length of the electrode, according to the invention.

Alternatively or additionally, in at least some embodiments, the lead is constructed so that the electrode 334 can be cut to a desired length, as illustrated in FIG. 3D. The electrode can be cut using a scalpel, shears, scissors, or any other suitable instrument. In some embodiments, the electrode can be cut to length, starting long and shortened if required as shown in FIG. 3D. In order to be cut, the conductor attached to the lead should be attached to a proximal portion of the lead so that the conductor/electrode is not severed when the electrode is cut. In addition, in at least some embodiments, the electrode 334 may be solid (for example, a solid cylinder of metal) so that, when cut, the lead is not open to inflow of fluid through the distal end of the lead. In at least some embodiments, the lead does not include a sheath, but does include an electrode that can be cut.

Many of the peripheral nerve targets are not deep within the tissue including, but not limited to, locations in the head such as the occipital nerve, the orbital nerve, or the trigeminal nerve. Hence a low profile lead body and electrode array may be preferred for these targets. A low profile lead configuration may also be highly beneficial for other stimulation targets that are only a few millimeters below the surface of the skin. In at least some embodiments, a low profile lead body with a diameter less than traditional SCS lead bodies is desirable. In particular, the distal end of the lead, where the electrode or electrode array resides, can be low profile and, in some instances, non-circular in cross-section. As an example, a low profile portion of a lead may have a diameter in the range of 0.020 inch-0.040 inch (0.051 to 0.10 cm) or in some cases less than 0.020 inch (0.51 cm).

Figures 4A, 4B, 4C, 4D, 4E:
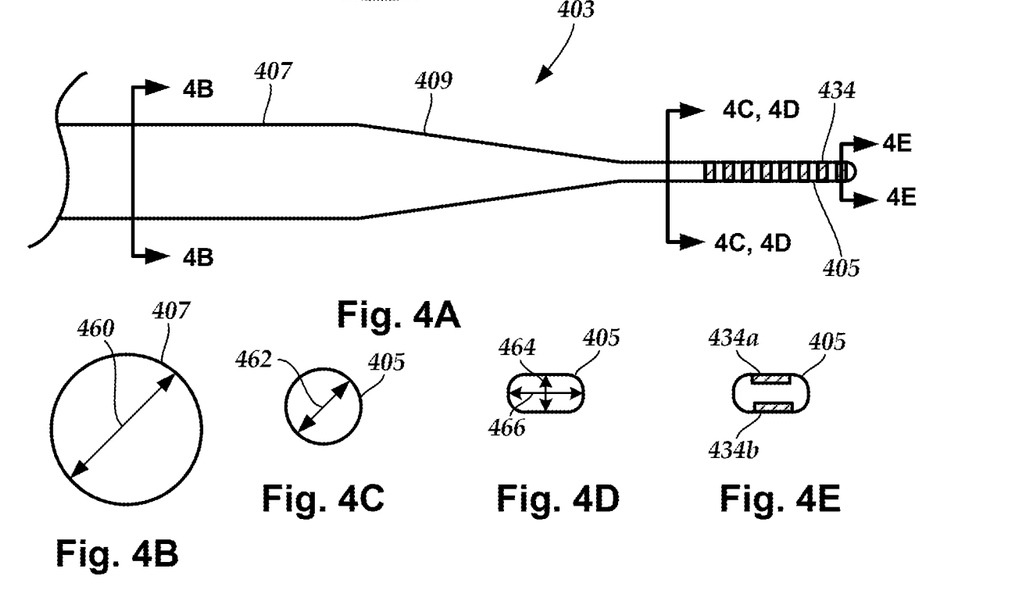
FIG. 4A is a schematic side view of a portion of one embodiment of a lead having a low-profile distal portion, according to the invention.
FIG. 4B is a lateral cross-section of a wider portion of the lead of FIG. 4A, according to the invention.
FIG. 4C is a lateral cross-section of one embodiment of the low-profile distal portion of the lead of FIG. 4A, according to the invention.
FIG. 4D is a lateral cross-section of another embodiment of the low-profile distal portion of the lead of FIG. 4A, according to the invention.
FIG. 4E is a lateral cross-section of the embodiment of the low-profile distal portion of the lead of FIG. 4D with segmented electrodes, according to the invention.

FIG. 4A illustrates one embodiment of a lead 403 with a distal portion 405 that has a smaller cross-section than a remainder 407 of the lead. The distal portion 405 includes one or more electrodes 434. FIG. 4B illustrates, in cross-section, the larger diameter 460 of the remainder 407 of the lead. FIGS. 4C and 4D illustrate, in cross-section, two embodiments of the low-profile distal portion 405. In FIG. 4C, the cross-section of the low-profile distal portion 405 is circular with a smaller diameter 462 than the remainder of the lead. In FIG. 4D, the cross-section of the low-profile distal portion 405 of the lead is square or rectangular (with or without rounded corners) or oval. In at least some embodiments, the low-profile distal portion 405 has a minor axis 464 and a major axis 466. At least the width of the minor axis 464 is smaller than the diameter 460 of the remainder 407 of the lead. The width of the major axis 466 may be equal to, or smaller than, the diameter 460 of the remainder of the lead.

In at least some embodiments, the low-profile distal portion 405 of the lead has a diameter 462, width of the minor axis 464, or width of the major axis 466 in the range of 0.020 inch-0.040 inch (0.051 to 0.10 cm). In at least some embodiments, the low-profile distal portion 405 of the lead has a diameter 462 or width of the minor axis 464 of no more than 0.020 inch (0.051 cm). In at least some embodiments, the width of the remainder 407 of the lead is at least 0.040 inch (0.10 cm).

In at least some embodiments, the electrodes 434 fully surround the perimeter of the distal portion 405 of the lead, as illustrated in FIG. 4A. In other embodiments, the electrodes 434 only partially surround (for example, no more than 75%, 50%, 34%, 25%, or less of) the perimeter of the lead body. In yet other embodiments, multiple segmented electrodes 434 can be disposed around the perimeter of the distal portion 405 of the lead similar to the segmented electrodes disclosed in U.S. Patent Applications Publication Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No.

8,483,237, all of which are incorporated herein by reference in their entireties. Such segmented electrodes can be used to provide directionality to the stimulation. As one example, segmented electrodes can be positioned on opposite sides of the distal portion 405 of the lead 403, as illustrated in FIG. 4E.

In addition, the sloping or diminishing region 409 between the distal portion 405 and the remainder 407 of the lead may reduce migration of the lead. Furthermore, the small, highly flexible lead body also helps to reduce or prevent migration as the mass of the lead body is lower and hence the momentum generated is smaller than a larger spinal cord stimulation lead. The smaller diameter or lower profile of the lead may also reduce ischemia due to the lead and arising from vessel compression.

Figure 5:
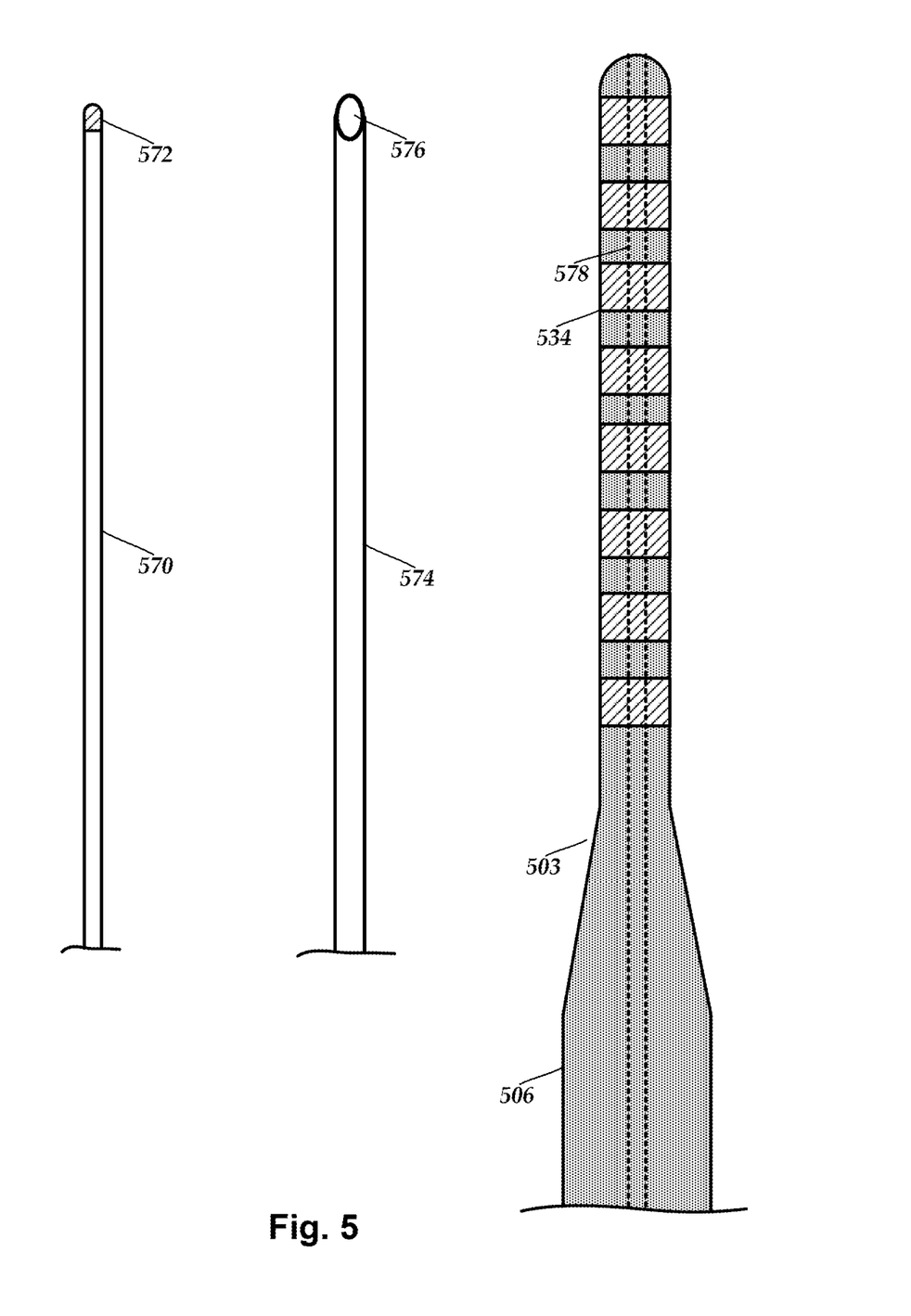
FIG. 5 is a schematic side view of one embodiment of components for a system, kit, or method for implanting a lead for stimulation of a peripheral nerve of a patient including an introducer, a guidewire, and a lead, according to the invention.

FIG. 5 illustrates another embodiment of a lead and related items for implanting the lead. A thin guidewire 570 with an electrode 572 can first be inserted to access the potential target prior to placement of a lead 503. The guidewire 570 can be implanted through an introducer 574, such as a small gauge needle. The guidewire 570 and mapping electrode 572 may be used to determine the length, width, depth, or volume (or any combination thereof) of the target stimulation area which may help inform the electrode length (for example, for a lead such lead 303 in FIGS. 3A-3D) or size of the electrode array of the lead.

In the illustrated embodiment, the guidewire 570 includes an electrode 572 disposed on, or near, a distal end of guidewire. A conductor (not shown) will extend along the guidewire 570 from the electrode 572 to a proximal end of the guidewire so that the guidewire can be coupled to a device for providing or receiving electrical signals from the electrode 572. Although a single electrode 572 is illustrated, in some embodiments the guidewire 570 includes two or more electrodes which may be electrically coupled together or may be independent of each other with separate conductors extending along the guidewire. Each of the electrodes can be a ring electrode, tip electrode, a segmented electrode, or any other suitable type of electrode. A lead with multiple electrodes can include a tip electrode, ring electrodes, or segmented electrodes or any combination thereof.

The introducer 574 defines a lumen 576 through which the guidewire 570 can be delivered. In at least some embodiments, the introducer 574 is 20 gauge (0.036" or 0.091 cm nominal outer diameter) or smaller. Advancing a small mapping guidewire 470 adjacent the peripheral nerve and moving the small mapping guidewire with respect to the peripheral nerve may be easier and less time consuming than using a lead for mapping. Furthermore, this guidewire can be steerable to allow for repositioning of the guidewire, as needed. Repositioning of the introducer 574 or guidewire 570 is easier and faster with a smaller introducer instead of the conventional larger lead and its introducer.

The guidewire 570 and its associated electrode 572 can be used to map or otherwise test the response of the patient tissue to electrical stimulation. Additionally or alternatively, the guidewire 570 and its associated electrode 572 can be used to map the electrical signals from patient tissue. In particular, the electrode 570 of the guidewire 572 can be used to map the space in and around the peripheral nerve. The mapping can be used to find a desirable location for lead placement or a desirable size for the electrode or electrode array.

In at least some embodiments, the electrical stimulation lead 503 includes a lumen 578 (such as a central lumen or any other lumen within the lead), sized to receive the guidewire 570, so that the lead can be inserted into the patient over the guidewire. The guidewire 570 can remain implanted or can be removed after implantation of the lead 503. In other embodiments, the guidewire 570 is removed prior to implantation of the electrical stimulation lead and the lead 503 is inserted using a lead introducer. In at least some embodiments, the introducer 574 can be sufficiently large that the lead 503 can be delivered through the introducer and over the guidewire 570.

The electrical stimulation lead 503 includes a lead body 506 and one or more electrodes 534. As examples, any of the leads 103, 303, 403 described herein can be used as lead 503. Any other suitable electrical stimulation lead, including those described in the references cited above, can also be used for lead 503.

Figure 6:
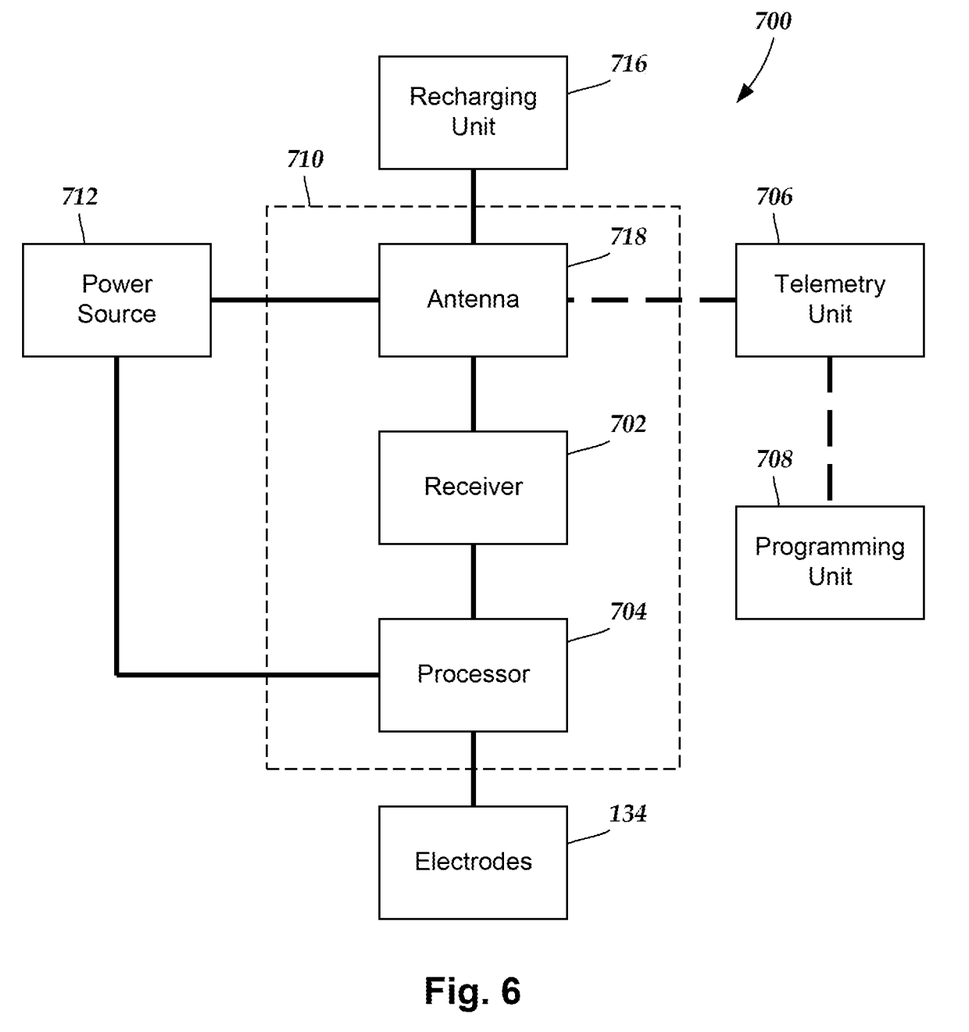
FIG. 6 is a schematic overview of one embodiment of components of an electrical stimulation system, according to the invention.

FIG. 6 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification and examples provide a description of the arrangement and use of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
a lead body having a proximal end portion and a distal end portion, wherein the distal end portion has a smaller lateral width in at least one direction than a remainder of the lead body;
a plurality of terminals disposed at the proximal end portion of the lead body;
a plurality of electrodes disposed at the distal end portion of the lead body; and
a plurality of conductors extending along the lead body and electrically coupling the plurality of terminals to the plurality of electrodes.

2. The electrical stimulation lead of claim 1, wherein the distal end portion has a circular cross-section.

3. The electrical stimulation lead of claim 2, wherein the distal end portion of the lead body of the electrical stimulation lead has a diameter of 0.020 inch or less.

4. The electrical stimulation lead of claim 3, wherein the remainder of the lead body of the electrical stimulation lead has a diameter of at least 0.040 inch.

5. The electrical stimulation lead of claim 1, Therein at least one electrode of the plurality of electrodes does not extend around a full perimeter of the distal end portion of the lead body of the electrical stimulation lead.

6. The electrical stimulation lead of claim 1, wherein the distal end portion has a cross-section with a major axis width and a minor axis width of different values.

7. The electrical stimulation lead of claim 6, wherein the minor axis width of the distal end portion of the lead body of the electrical stimulation lead has a value of 0.020 inch or less.

8. The electrical stimulation lead of claim 1, wherein the distal end portion has a square or rectangular cross-section with or without rounded corners.

9. The electrical stimulation lead of claim 1, wherein the distal end portion has an oval cross-section.

10. The electrical stimulation lead of claim 1, wherein the lead body also has a diminishing width portion between the distal end portion and the remainder of the lead body.

11. An electrical stimulation lead, comprising:
a lead body having a proximal end portion and a distal end portion, wherein the distal end portion has a smaller lateral width in at least one direction than a remainder of the lead body, wherein the distal end portion has a cross-section with a major axis width and a minor axis width of different values;
at least one terminal disposed at the proximal end portion of the lead body;
at least one electrode disposed at the distal end portion of the lead body; and
at least one conductor extending along the lead body and electrically coupling the at least one terminal to the at least one electrode.

12. The electrical stimulation lead of claim 11, wherein the minor axis width of the distal end portion of the electrical stimulation lead has a value of 0.020 inch or less.

13. The electrical stimulation lead of claim 11, wherein the at least one electrode is a plurality of electrodes.

14. The electrical stimulation lead of claim 11, wherein at least one of the at least one electrode does not extend around a full perimeter of the distal end portion of the lead body of the electrical stimulation lead.

15. The electrical stimulation lead of claim 11, wherein the distal end portion has a rectangular cross-section with or without rounded corners.

16. The electrical stimulation lead of claim 11, Wherein the distal end portion has an oval cross-section.

17. An electrical stimulation lead, comprising:
a lead body having a proximal end portion and a distal end portion, wherein the distal end portion has a smaller lateral width in at least one direction than a remainder of the lead body, Wherein the distal portion has a cross-section with a major axis width and minor axis width of different values, wherein the major axis width is equal to a diameter of the remainder of the lead body;

at least one terminal disposed at the proximal end portion of the lead body;

at least one electrode disposed at the distal end portion of the lead body; and at least one conductor extending along the lead body and electrically coupling the at least one terminal to the at least one electrode.

18. The electrical stimulation lead of claim 11, wherein the lead body also has a diminishing width portion between the distal end portion and the remainder of the lead body.

19. The electrical stimulation lead of claim 11, wherein the minor axis width is 0.020 inch or less.

20. The electrical stimulation lead of claim 19, wherein the remainder of the lead body of the electrical stimulation lead has a diameter of at least 0.040 inch.

* * * * *